United States Patent
Harichian et al.

(10) Patent No.: US 8,822,711 B2
(45) Date of Patent: *Sep. 2, 2014

(54) METHOD FOR PREPARING FATTY ACYL AMIDO CARBOXYLIC ACID BASED SURFACTANTS

(75) Inventors: Bijan Harichian, Trumbull, CT (US); Van Au, Trumbull, CT (US); Badreddine Ahtchi-Ali, Trumbull, CT (US); John Robert Winters, Trumbull, CT (US); Peter Anthony Divone, Sr., Trumbull, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 304 days.

This patent is subject to a terminal disclaimer.

(21) Appl. No.: 13/343,726

(22) Filed: Jan. 5, 2012

(65) Prior Publication Data

US 2013/0030202 A1    Jan. 31, 2013

Related U.S. Application Data

(63) Continuation-in-part of application No. 13/192,489, filed on Jul. 28, 2011.

(51) Int. Cl.
*C07C 231/00*    (2006.01)

(52) U.S. Cl.
USPC .............................................. 554/69; 554/68

(58) Field of Classification Search
USPC .................................................. 554/69, 68
See application file for complete search history.

(56) References Cited

U.S. PATENT DOCUMENTS

| | | | |
|---|---|---|---|
| 3,836,551 A | 9/1974 | Schroeder et al. | |
| 5,194,639 A * | 3/1993 | Connor et al. | 554/66 |
| 5,529,712 A | 6/1996 | Sano | |
| 5,646,318 A * | 7/1997 | Dery et al. | 554/69 |
| 5,710,295 A | 1/1998 | Woodbury et al. | |
| 5,723,673 A * | 3/1998 | Kao et al. | 564/487 |
| 5,767,059 A | 6/1998 | Umemoto et al. | |
| 6,703,517 B2 | 3/2004 | Hattori et al. | |
| 6,958,085 B1 | 10/2005 | Parrish | |
| 7,439,388 B2 | 10/2008 | Harichian et al. | |
| 2002/0028954 A1 | 3/2002 | Khoury | |
| 2004/0063980 A1 | 4/2004 | Raths | |
| 2005/0176615 A1 | 8/2005 | Kinoshita | |
| 2006/0090644 A1 | 5/2006 | Sirkar | |
| 2006/0239952 A1 | 10/2006 | Hattori | |

FOREIGN PATENT DOCUMENTS

| | | |
|---|---|---|
| DE | 2004099 | 1/1970 |
| DE | 4408957 A1 | 3/1994 |
| EP | 1801194 A1 | 6/2007 |
| GB | 1337782 | 11/1973 |
| JP | 5758653 | 9/1980 |
| WO | WO2008019807 A1 | 2/2008 |

OTHER PUBLICATIONS

Chen et al, Vinyl Carboxylate an Acylating Reagent for Selective Acylation of Amines and Diols, Tetrahedron Letters, 1994, vol. 35 No. 21, pp. 3583-3584.
Falk et al., The Preparation and Properties of Surface-Active N-Acylamino-Methanesulfonates, Journal of America Oil Chem Society, Apr. 1958, vol. 35 No. 4, pp. 171-176.
Martin et al., Application of AlMe3-Mediated Amidation Reactions to Solution Phase Peptide Synthesis, Tetrahedron Letters, 1998, vol. 39, pp. 1517-1520.
PCT International Search Report in PCT application PCT/EP2012/064772 dated Dec. 11, 2012 with Written Opinion.
PCT International Search Report in PCT application PCT/EP2012/064769 dated Dec. 7, 2012 with Written Opinion.
PCT International Search Report in PCT application PCT/EP2012/064771 dated Dec. 10, 2012 with Written Opinion.
PCT International Search Report in PCT application PCT/EP2012/064770 dated Dec. 10, 2012 with Written Opinion.
PCT International Search Report in PCT application PCT/EP2012/064768 dated Nov. 7, 2012 with Written Opinion.
Co-Pending U.S. Appl. No. 13/192,489, filed 7/28/11; titled: "Method for Preparing Fatty Acyl Amido Carboxylic Acid Based Surfactants".
Co-Pending U.S. Appl. No. 13/192,490, filed Jul. 28, 2011; titled General Method for Preparing Fatty Acyl Amido Based Surfactants.
Co-Pending; U.S. Appl. No. 13/192,492, filed Jul. 28, 2011; titled "Fatty Acyl Amido Based Surfactant Concentrates".
Co-Pending; U.S. Appl. No. 61/512,434, filed Jul. 28, 2011; titled "Concentrated Fatty Acyl Amido Surfactant Compositions".
Co-Pending; U.S. Appl. No. 13/343,727, filed Jan. 5, 2012; titled "General Method for Preparing Fatty Acyl Amido Based Surfactants".
Co-Pending ; U.S. Appl. No. 13/343,728, filed Jan. 5, 2012; titled "Amino Acid Salt Containing Compositions".
Co-Pending; U.S. Appl. No. 13/343,730, filed Jan. 5, 2012; titled "Fatty Acyl Amido Based Surfactant Concentrates".
Co-Pending; U.S. Appl. No. 13/343,731, filed Jan. 5, 2012; titled "Concentrated Fatty Acyl Amido Surfactant Compositions".

* cited by examiner

*Primary Examiner* — Deborah D Carr

(74) *Attorney, Agent, or Firm* — Ronald A. Koatz

(57) ABSTRACT

A process is provided for preparing $C_8$-$C_{22}$ acyl glycinate acid or salt thereof via reacting and heating reacting a mixture of glycine or salt thereof with a fatty acid ester in a medium selected from the group consisting of glycerol, propylene glycol and combinations thereof, and wherein the mixture has a pKa ranging from 9.5 to 13.

21 Claims, No Drawings

METHOD FOR PREPARING FATTY ACYL AMIDO CARBOXYLIC ACID BASED SURFACTANTS

CROSS-REFERENCES TO RELATED APPLICATIONS

This application is a continuation-in-part of Ser. No. 13/192,489 filed Jul. 28, 2011.

BACKGROUND OF THE INVENTION

1. Field of the Invention

The invention concerns a process for producing fatty acyl amido carboxylic acid based surfactants.

2. The Related Art

Fatty acyl amido carboxylic acid salts are desirable surfactants. They have good water solubility, good detergency and foaming properties. Most especially they are mild to the skin. Unfortunately the amount of and extent of their usage is limited because they are expensive to produce.

The most traditional and present commercial route to fatty acyl amido carboxylic salts is found in U.S. Pat. No. 6,703,517 (Hattori et al.). Synthesis is achieved by reacting the amino acid with activated fatty acid derivatives, especially fatty acyl chlorides. The process requires a mole equivalent of alkali to remove the hydrogen chloride byproduct of the reaction. There are evident waste disposal issues with the byproducts and the added cost of chloride is not fully recoverable.

U.S. Pat. No. 7,439,388 B2 (Harichian et al.) describes a process wherein primary amido alcohol is oxidized to a corresponding amido carboxylic acid in high yield. Illustrative is the conversion of cocomonoethanolamide to N-cocoylglycine, mediated by use of a hindered nitroxide catalyst.

WO 2008/019807 A1 (Clariant International Ltd.) describes a process for preparing acyl glycinates by oxidation of fatty acid monoethanolamides using a transition group metal catalyst, particularly a gold on titanium dioxide nano-sized catalyst.

Direct esterification and interesterification are routes which also have been previously investigated. US Patent Application Publication No. 2006/0239952 A1 (Hattori) describes a reaction between a neutral amino acid and a long chain fatty acid catalyzed by an alkaline substance such as sodium hydroxide or potassium hydroxide. For instance, the reaction between glycine and lauric acid produces the acylated products lauroylglycine and lauroylglycylglycine. Significant byproducts include the non-acylated forms such as glycylglycine and glycyldiketopiperazine, as well as unreacted glycine. The reaction is said to be highly efficient (yield of the acylated forms) but this results because the ratio of lauric acid starting material to glycine is extremely high.

GB 1 337 782 (Rohm Gmbh) describes an interesterification process for the preparation of salts of N-acylaminocarboxylic acids. A carboxylic acid or an amide thereof is reacted with an aminocarboxylic acid containing at least three carbon atoms, the reaction being done in the presence of at least a stoichiometric amount (based upon the aminocarboxylic acid) of salt-forming cations. Among the aminocarboxylic acids, only glycine was said to be unusable because the process resulted in considerable resinification. Higher homologues of glycine were said, however, to react well; these included alanine, beta-alanine, sarcosine, valine, leucine, phenyl glycine and phenyl alanine. Solvents such as water or organic solvents such as dimethylformamide were said to be necessary.

DE 44 08 957 A1 (BASF AG) reports preparation of N-acyl aminocarboxylic acids by reaction of a suspension of solid anhydrous alkali metal salts of aminocarboxylic acids and an appropriate carboxylic acid or ester. Catalytic amounts of strong base are added to the suspension to promote the reaction. Illustrative is the reaction of equimolar amounts of lauric acid and anhydrous sodium sarcosine heated together molten at 200° C. in the presence of a molar equivalent of sodium hydroxide. Although the yields are high, the resultant product is highly colored.

Japanese Patent Application 57/058,653 (Ota) reports a process for producing a N-acylamino acid by reacting the corresponding amino acid with an ester. Illustrative esters include methyl laurate, methyl stearate and fatty acid glyceride esters such as triacetin, trilaurin and tristearin. Although a solvent was said not always to be necessary, all the examples utilize polar solvents such as acetonitrile, dimethyl sulfoxide or N,N-dimethylformamide.

None of the known esterification or interesterification processes are without a disadvantage. Many require relatively high temperatures and/or strong alkali to progress the reaction. These conditions promote side reactions of the amino acids with themselves rather than with the fatty acylating reagent. These competing reactions squander expensive amino acid starting reagent and require removal cleanup steps. Yields are also adversely affected. Furthermore, the necessary conditions for reaction in the known art are too harsh for the simplest of amino acids, i.e. glycine.

SUMMARY OF THE INVENTION

A process for the preparation of a $C_8$-$C_{22}$ acyl glycinate acid or salt thereof is provided which includes:
(i) reacting a mixture of glycine or salt thereof with a fatty acid ester in a medium selected from the group consisting of glycerol, propylene glycol and combinations thereof, and wherein the mixture has a pKa ranging from 9.5 to 13;
(ii) heating the mixture to form the $C_8$-$C_{22}$ acyl glycinate acid or salt thereof; and
(iii) recovering the $C_8$-$C_{22}$ acyl glycinate acid or salt thereof in a reaction resultant mass.

DETAILED DESCRIPTION OF THE INVENTION

Now a relatively mild interesterification reaction has achieved good yields of $C_8$-$C_{22}$ acyl glycinate free acids or salts thereof. An important element in achieving the product is use of glycerol (glycerin), propylene glycol or combinations as a reaction medium.

Advantageously, the reaction medium will be substantially free of water. By substantially free of water is meant amounts from 0 to 10%, preferably from 0 to 5%, more preferably from 0 to 3%, still more preferably from 0 to 1%, and especially from 0.05 to 1% by weight of water. Water of hydration (such as found in glycine monohydrate) is not considered to count as part of water present in the reaction medium.

The reaction mixture desirably should have a pKa at 25° C. ranging from 9.5 to 13, and preferably from 10.5 to 12.

A first reagent is that of glycine or salt thereof. Suitable salts include sodium and potassium salts of the glycine. The reagent may either be in an anhydrous or hydrated form. Glycine monohydrate is particularly suitable.

A second reagent is a fatty acid ester. The term "fatty acid" is herein defined as an 8 to 22 carbon carboxylic radical containing material that may be saturated, unsaturated, branched, unbranched or a combination thereof.

A variety of fatty acid esters may be suitable as co-reactants. Most preferably are the $C_1$-$C_3$ alkyl esters of a $C_8$-$C_{22}$ fatty acid. Illustrative are methyllaurate, methyloleate, methylinoleate, methylmyristate, methylstearate, methyl palmitate, ethyllaurate, ethyloleate, ethyllinoleate, ethylmyristate, ethylstearate, ethylpalmitate, n-propyllaurate, n-propyloleate, n-propyllinoleate, isopropyllaurate, isopropyloleate, isopropyllinoleate, isopropylmyristate, isopropylstearate, isopropylpalmitate and mixtures thereof. Particularly suitable is methyl cocoate.

The $C_1$-$C_3$ alkyl esters of $C_8$-$C_{22}$ fatty acids may be generated from triglycerides by hydrolysis with a respective $C_1$-$C_3$ alkanol. Most suitable as the alkanol is methanol. Amongst useful but not exclusive triglycerides are coconut oil, corn oil, palm kernel oil, palm oil, soybean oil, sunflowerseed oil, cottonseed oil, rapeseed oil, canola oil, castor oil and mixtures thereof. Most preferred is coconut oil.

An alternative fatty acid ester suitable as a co-reactant in the process of this invention are the glyceride esters. These glycerides may be selected from monoglycerides, diglycerides, triglycerides and mixtures thereof. Illustrative monoglycerides are monoglyceryl laurate, monoglyceryl oleate, monoglyceryl linoleate, monoglyceryl myristate, monoglyceryl stearate, monoglyceryl palmitate, monoglyceryl cocoate and mixtures thereof. Illustrative diglycerides include glyceryl dilaurate, glyceryl dioleate, glyceryl dilinoleate, glyceryl dimyristate, glyceryl distearate, glyceryl diisostearate, glyceryl dipalmitate, glyceryl cocoate, glyceryl monolaurate monomyristate, glyceryl monolaurate monopalmitate and mixtures thereof. Illustrative but non-limiting triglycerides include oils and fats such as coconut oil, corn oil, palm kernel oil, palm oil, soybean oil, cottonseed oil, rapeseed oil, canola oil, sunflowerseed oil, sesame oil, rice oil, olive oil, tallow, castor oil and mixtures thereof. Most preferred is coconut oil. Use of mono-, di- and tri-glycerides as the co-reactant has an advantage over the $C_1$-$C_3$ alkyl esters of $C_8$-$C_{22}$ fatty acids. The latter are generally made from breakdown of triglycerides. Conversion from the triglycerides adds an extra step to the process. A disadvantage of using the mono-, di- and tri-glycerides as starting co-reactant is the albeit good but slightly lower yields of resultant acyl glycinate product.

Schematically the process of preparing $C_8$-$C_{22}$ acyl glycinate acids or salts thereof with a $C_1$-$C_3$ alkyl ester of a $C_8$-$C_{22}$ fatty acid (hereinafter the "monoester route") corresponds to the following reaction scheme (which optionally includes a triglyceride precursor for illustrative purposes).

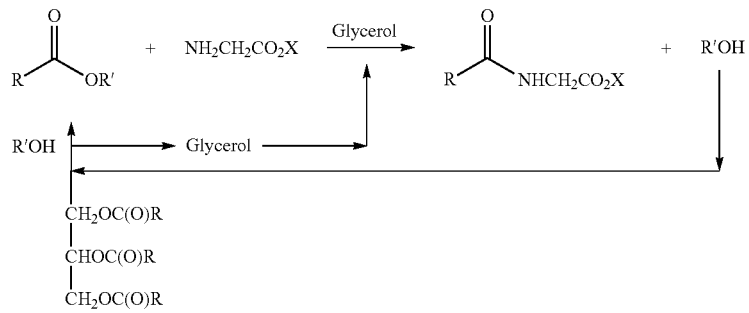

wherein R is a $C_7$-$C_{21}$ radical selected from the group consisting of saturated and unsaturated alkyl groups and mixtures thereof; and R' is a $C_1$-$C_3$ alkyl; and X is a cationic counterion, preferably sodium or potassium cations. Most preferably, R' is a methyl group.

Schematically, the process of preparing $C_8$-$C_{22}$ acyl glycinate acids or salts thereof directly with a triglyceride as co-reactant corresponds to the following reaction scheme.

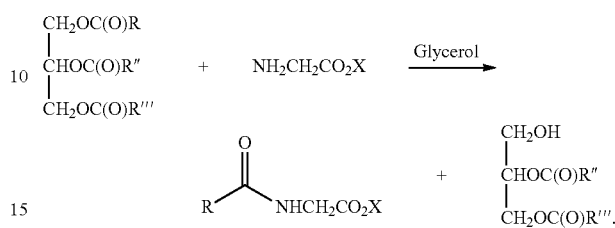

wherein R is a $C_7$-$C_{21}$ radical selected from the group consisting of saturated and unsaturated alkyl groups and mixtures thereof; R" and R'" independently are selected from $C_7$-$C_{21}$ radicals which may be the same or different, hydrogen and mixtures thereof; and X is a cationic counterion, preferably sodium or potassium cations. Most preferably, R is a $C_{11}$ radical.

An advantage of the present process over the traditional Schotten-Bauman acyl halide route is that unsaturated fatty esters such as oleyl and linoleyl esters can be tolerated. These unsaturated acids will not undergo decomposition or generate color bodies as happens in those reactions of the known art. Minimum byproducts are produced in the process. We have found no evidence of a glycylglycine or glycyldiketopiperazine. Neither are there any waste streams. Glycerol liberated from the triglyceride can be utilized as a reaction medium. The alkanol (for instance methanol) that distills off from the main reaction of the monoester route can be fed back into the triglyceride hydrolysis reaction to form new methyl fatty acid ester.

Relative molar amounts of glycine or salt thereof to fatty acid ester may range from about 3:1 to about 1:3, preferably from about 2:1 to about 1:1, more preferably from 1.3:1 to 1.05:1.

Glycerol, propylene glycol or mixtures of these liquids will be the reaction medium. The relative mole ratio of glycerol or propylene glycol medium to glycine or salt thereof may range from about 8:1 to about 1:1, preferably from about 6:1 to about 1:1, and more preferably from about 2:1 to 1:1. Generally, the total amount of glycerol, propylene glycol and mixtures thereof will range from 50 to 100%, preferably 80 to 100%, and optimally 98 to 100% by weight of the medium.

Temperature conditions for the reaction may range from about 50° C. to about 150° C., preferably from about 80° C. to about 140° C., and optimally from about 110° C. to about 130° C.

Basic metal salt containing catalysts may be usefully present to improve reaction speeds and conversion levels. Particularly useful are alkaline and alkaline earth metal containing hydroxides, phosphates, sulphates and oxides including calcium oxide, magnesium oxide, barium oxide, sodium oxide, potassium oxide, calcium hydroxide, magnesium hydroxide, calcium phosphate, magnesium phosphate and mixtures thereof. Most suitable are calcium oxide and magnesium oxide, with the former being preferred. Amounts of the basic metal salt catalyst may range from about 1 to about 20%, preferably from about 1 to about 10%, more preferably from about 1.5 to 5% by weight of glycine starting material present in the reaction.

Buffering compounds may also in some embodiments have utility to improve conversions and reaction times of the present invention. Suitable buffers include trisodium phosphate, disodium hydrogen phosphate, sodium citrate, sodium carbonate, sodium bicarbonate, sodium borate and mixtures thereof. Particularly useful is trisodium phosphate. Amounts of the buffer may range from about 1 to about 30% by weight of glycine starting material present in the reaction. Preferably the amount is from about 5% to about 15% by weight of the glycine starting material present in the reaction.

Advantageously, distillation of the alkanol (e.g. methanol) in the monoester route can be done under atmospheric as well as reduced pressure conditions.

The reaction products for many purposes need not be isolated. For instance, glycerol may not need to be separated where the acyl glycinate salts are intended for personal care products such as body washes, toilet bars, shampoos or even skin lotions. Glycerol is useful in these products as a moisturizer. In circumstances where glycerol, unreacted starting materials or the minor byproducts are undesirable, the resultant reaction mass can be further processed. For instance, the mass can be treated with ethanol which precipitates out the acyl glycinate salt or with acidification the free acid form but retains glycerol and unreacted starting materials solubilized within the ethanol. Upon separation of the acyl glycinate product, the unreacted starting materials and glycerol can be recycled for further reaction by evaporation (e.g. distillation) of the ethanol.

Colored byproducts ordinarily generated in previously known routes to acyl glycinate salts are avoided through the present process. Confirmation of the absence of colored species such as glycylglycine and glycyldiketopiperazine has been established through chromatography and/or mass spectroscopy analytical procedures. Yet, perhaps the best indicator of the clean nature of products formed in the process is the visual lack of dark coloration (e.g. absence of tan, brown, or even green/blue heretofore evident from other glycinate forming pathways). Subsequent to heating step (ii), the hot liquid resultant mass of reaction product bearing acyl glycinate product and glycerol is removed from the reactor and forms a semi-solid. Color of this mass is evaluated by the Hunter Lab Color Scale. The resultant mass from the reaction can vary in color from white to slightly off-white. On the Hunter scale, the key parameter will be the L value which is a reflectance measure of brightness. L should range between 70 and 100, preferably from 75 to 100, and optimally from 90 to 100. Desirably, the b value can also be considered. The "b" may range from 0 to 20, preferably from 0 to 15 and optimally from 0 to 3. Of less impact is the "a" value, which may range from −2 to 8, preferably −1 to 5 and optimally from 0 to 4.

Values for the present invention were established by comparing the reaction resultant mass color (cooled at the end of the process) with a Color Metric Converter chart available online at http://www.colorpro.com/info/tools/convert.htm.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

EXAMPLE 1

Cocoyl Glycinate Via Monoester Route

A 250 ml 3-neck glass reactor vessel was used to conduct a series of comparative experiments. A central neck was fitted with a stirring rod with Teflon® blade at one end and a motor for rotating the rod at a second end. A second neck of the reactor was fitted with a water-cooled condenser leading to a Dean-Stark trap for collecting methanol generated in the interesterification reaction. The third neck was fitted with a thermometer attached to a temperature control device. The reactor was externally heated in a glas-col heating mantle. In experiment 1, the reactor was charged with 25 g glycerol, 0.41 g calcium oxide, 17.5 g sodium glycine, and 39 g cocoyl methyl ester. Initially two phases were present in the reactor. The reactants were then heated at 120° C. for 2 hours under constant stirring and dry nitrogen. The reactor contents were then cooled to a point just above solidification and removed from the reactor. The resultant mass was a white colored paste. Analysis by liquid chromatography revealed an approximately 87% yield (based on starting glycine) of sodium cocoyl glycinate.

The resultant mass contained 50.3% sodium cocoyl glycinate, 7.2% $C_8$-$C_{18}$ fatty acids, 34.1% glycerol, 1.6% glycine, less than 1.0% methyl cocoate, and the remainder calcium oxide and other minor materials.

Via liquid chromatography/mass spec analysis, the sodium cocoyl glycinate contained the following fatty acid chain length distribution based on % amounts in the total resultant mass: 5.0% $C_8$, 3.8% $C_{10}$, 27.4% $C_{12}$, 9.7% $C_{14}$, 4.5% $C_{16}$ and 6.9% $C_{18}$. The $C_{18}$ glycinate was a mixture of stearic, oleic and linoleic isomers. The unsaturated $C_{18}$ compounds survived the reaction conditions in contrast to their absence under conditions of the alternate acyl chloride route.

A series of further experiments were conducted to evaluate the importance of catalyst, buffer, reaction times and temperatures. These experiments are recorded in Table I. Reactants and conditions are identical to experiment 1, except where otherwise indicated through footnotes for Table I.

TABLE I

| Experiment No. | Glycerol | Calcium Oxide | Buffer | Reaction Mixture pKa | Reaction Time (Hours) | Yield (%) | Temp. (°C.) | Hunter Lab Color Scale | | |
|---|---|---|---|---|---|---|---|---|---|---|
| | | | | | | | | L | a | b |
| 1 | Yes | Yes | None | 9.6 | 2 | 87 | 120 | 95.28 | 0.56 | 12.98 |
| 2 | Yes | Yes | Yes[1] | 9.6 | 2 | 95+ | 120 | 93.12 | −0.52 | 2.41 |
| 3 | Yes | Yes[2] | None | 9.6 | 2 | 95+ | 120 | 93.12 | −0.52 | 2.41 |
| 4 | Yes | None | None | 9.6 | 4-5 | 40-50 | 120-140 | 95.28 | 0.56 | 12.98 |
| 5 | None | None | None | 9.6 | 5 | <10 | 110-150 | 46.2 | 9.21 | 33.05 |
| 6 | None | Yes | None | 9.6 | 2 | <5 | 120 | 46.2 | 9.21 | 33.05 |
| 7 | None | Yes | Yes | 9.6 | 2 | <5 | 120 | 46.2 | 9.21 | 33.05 |
| 8 | Yes | Yes[3] | Yes | 9.6 | 2 | 75 | 120 | 93.12 | −0.52 | 2.41 |
| 9 | Yes | Yes[4] | Yes | 9.6 | 2 | 30-50 | 110-120 | 93.53 | −0.12 | 6.07 |
| 10 | Yes | Yes | None | 10.2 | 5 | 84 | 120 | 93.12 | −0.52 | 2.41 |
| 11 | Yes | Yes | Yes[6] | 9.8 | 5 | 94 | 120 | 93.12 | −0.52 | 2.41 |
| 12 | Yes | Yes | Yes | 9.74 | 2 | 89 | 120 | 93.12 | −0.52 | 2.41 |
| 13 | Yes | Yes | Yes | 7.6 | 2 | 0 | 120 | 68.93 | 12.44 | 36.72 |
| 14 | Yes | Yes | Yes | 7.7 | 2 | 0 | 120 | 69.00 | 12.50 | 37.00 |
| 15 | Yes | Yes | Yes | 8.9 | 2 | 0 | 120 | 69.10 | 12.60 | 37.01 |

[1]Trisodium phosphate at 1.5 g.
[2]Doubled CaO to 0.82 g.
[3]Magnesium oxide substitute for calcium oxide at 0.41 g.
[4]Zinc oxide replacement for calcium oxide at 0.41 g.
[5]Propylene glycol replaced glycerol at 25 g.
[6]Trisodium phosphate doubled to 3.0 g.

Experiments 5-7 demonstrate that in the absence of glycerol, hardly any sodium cocoyl glycinate is formed. From these experiments it is clear that the medium is the crucial aspect in driving good conversions. Glycerol is best and propylene glycol is second best but also useful.

Experiments 13-15 demonstrate that reactions run at a pKa substantially lower than 9.5 do not result in any glycinate product. Zero yields were noted at pKa of 7.6, 7.7 and 8.9.

EXAMPLE 2

A series of different reaction mediums were evaluated. The experiments were conducted with reactants and conditions identical to experiment 1, except where otherwise indicated as footnotes to Table II.

TABLE II

| Experiment No. | Medium[7] | Calcium Oxide | Buffer | Reaction Mixture pKa | Reaction Time (Hours) | Temp. (°C.) | Yield (%) | Hunter Lab Color Scale | | |
|---|---|---|---|---|---|---|---|---|---|---|
| | | | | | | | | L | a | b |
| 16 | Methanol | Yes[8] | None | 9.6 | 2 | 120 | <5 | 93.39 | 2.01 | 24.30 |
| 17 | Ethanol | Yes | Yes | 9.6 | 4.5 | 80 | <5 | 93.39 | 2.01 | 24.30 |
| 18 | Isopropyl Alcohol | Yes | Yes | 9.6 | 5 | 90 | <5 | 93.39 | 2.01 | 24.30 |
| 19 | Toluene | Yes | None | 9.6 | 5 | 110 | <5 | 93.39 | 2.01 | 24.30 |
| 20 | Isoamyl Alcohol | Yes | Yes[9] | 9.6 | 5 | 120 | <5 | 93.39 | 2.01 | 24.30 |
| 21 | Water | Yes | None | 9.6 | 3 | 100 | <5 | 68.93 | 12.44 | 36.72 |

[7]Amount of the medium was 100 g.
[8]Doubled CaO to 0.82 g.
[9]Trisodium phosphate doubled to 3.0 g.

Based on the results reported in Table II, it is evident that methanol, ethanol, isopropyl alcohol, toluene, isoamyl alcohol and water were ineffective in providing any reasonable conversion of reactants into sodium cocoyl glycinate. Only glycerol, and to a slightly lesser extent, propylene glycol were effective at driving the reactions to high conversions.

EXAMPLE 3

Cocoyl Glycinate via Triglycerides

A 250 ml 3-neck glass reactor vessel was used to conduct a series of comparative experiments. A central neck was fitted with a stirring rod with Teflon® blade at one end and a motor for rotating the rod at a second end. A second neck of the reactor was fitted with a water-cooled condenser leading to a Dean-Stark trap for collecting distillates generated in the interesterification reaction. The third neck was fitted with a thermometer attached to a temperature control device. The reactor was externally heated in a glas-col heating mantle. In experiment 1, the reactor was charged with 25 g glycerol, 17.5 g Na glycine, 0.41 g calcium oxide, 3 g sodium phosphate (buffer), and 41.2 g coconut oil. Initially two phases were present in the reactor. The reactants were then heated at 130° C. for 2 hours under constant stirring. The reactor contents were then cooled to a point just above solidification and removed from the reactor. The resultant mass was a white colored paste. Analysis by liquid chromatography revealed an approximately 92.7% yield (based on starting glycine) of sodium cocoyl glycinate. This experiment is identified as number 22 in Table III. Experiments 23-25 were done with reactants and under conditions identical to experiment 22, except where otherwise noted in the Table.

TABLE III

| Exper. No. | Calcium | | | Reaction Mixture | Reaction Time | Yield | Temp. | Hunter Lab Color Scale | | |
| | Glycerol | Oxide | Buffer | Triglyceride | pKa | (Hours) | (%) | (° C.) | L | a | b |
|---|---|---|---|---|---|---|---|---|---|---|---|
| 22 | Yes | Yes | Yes | Coconut Oil | 9.6 | 2 | 92.7 | 130 | 95.20 | 0.56 | 12.98 |
| 23 | Yes | Yes | Yes | Coconut Oil | 9.6 | 5 | 72 | 120 | 95.06 | −0.27 | 11.98 |
| 24 | Yes | Yes | None | Coconut Oil | 9.6 | 5 | 91.8 | 120-130 | 93.53 | −0.12 | 6.07 |
| 25 | Yes | Yes | Yes | Corn Oil | 9.6 | 5 | 60 | 120 | 90.10 | 1.34 | 39.74 |

Experiment 23 reveals that yields can vary with reaction time and temperature. The absence of buffer as in experiment 24 did not affect product yield. Corn oil is a triglyceride also found operative although yields were lower than with coconut oil. See experiment 25.

While the invention has been described in detail with reference to specific embodiments thereof, it will be apparent to one skilled in the art that various changes and modifications can be made therein without departing from the spirit and scope thereof.

What is claimed is:

1. A process for the preparation of a $C_8$-$C_{22}$ acyl glycinate acid or salt thereof comprising:
   (i) reacting a mixture of glycine or salt thereof with a fatty acid ester in a medium selected from the group consisting of glycerol, propylene glycol and combinations thereof, and wherein the mixture has a pKa ranging from 9.5 to 13;
   (ii) heating the mixture to form the $C_8$-$C_{22}$ acyl glycinate acid or salt thereof; and
   (iii) recovering the $C_8$-$C_{22}$ acyl glycinate acid or salt thereof in a reaction resultant mass.

2. The process according to claim 1 wherein the fatty acid ester is a $C_1$-$C_3$ alkyl ester of a $C_8$-$C_{22}$ fatty acid or a glyceride ester selected from mono-, di- or triglyceride.

3. The process according to claim 1 wherein the fatty acid ester is a $C_1$-$C_3$ alkyl ester of a $C_8$-$C_{22}$ fatty acid selected from the group consisting of methyllaurate, methyloleate, methylinoleate, methylmyristate, methylstearate, methylpalmitate, ethyllaurate, ethyloleate, ethyllinoleate, ethylmyristate, ethylstearate, ethylpalmitate, n-propyllaurate, n-propyloleate, n-propyllinoleate, isopropyllaurate, isopropyloleate, isopropyllinoleate, isopropylmyristate, isopropylstearate, isopropylpalmitate and mixtures thereof.

4. The process according to claim 1 wherein the fatty acid ester is a triglyceride selected from the group consisting of coconut oil, corn oil, palm kernel oil, palm oil, soybean oil, cottonseed oil, rapeseed oil, canola oil, sunflowerseed oil, sesame oil, rice oil, olive oil, tallow, castor oil and mixtures thereof.

5. The process according to claim 1 wherein the medium is glycerol.

6. The process according to claim 1 further comprising a basic metal salt containing catalyst.

7. The process according to claim 6 wherein the basic metal salt containing catalyst is selected from the group consisting of alkaline or alkaline earth metal containing hydroxides, phosphates, sulphates and oxides.

8. The process according to claim 6 wherein the basic metal salt containing catalyst is selected from the group consisting of calcium oxide, magnesium oxide, barium oxide, sodium oxide, potassium oxide, calcium hydroxide, magnesium hydroxide, calcium phosphate, magnesium phosphate and mixtures thereof.

9. The process according to claim 6 wherein the basic metal salt containing catalyst is calcium oxide.

10. The process according to claim 1 wherein the medium and glycine starting material or a salt thereof are present in a relative mole ratio ranging from about 8:1 to about 1:1.

11. The process according to claim 1 wherein the medium and glycine starting material or a salt thereof are present in a relative mole ratio ranging from about 6:1 to about 1:1.

12. The process according to claim 1 wherein the mole ratio of glycine starting material or salt thereof relative to the fatty acid ester ranges from about 3:1 to about 1:3.

13. The process according to claim 1 wherein the mole ratio of glycine starting material or salt thereof relative to the fatty acid ester ranges from 1.3:1 to 1.05:1.

14. The process according to claim 1 wherein heating the mixture is at a temperature ranging from about 50° C. to about 150° C.

15. The process according to claim 1 wherein heating the mixture is at a temperature ranging from about 80° C. to about 140° C.

16. The process according to claim 1 further comprising presence of a buffering agent.

17. The process according to claim 16 wherein the buffering agent is selected from the group consisting of trisodium phosphate, disodium hydrogen phosphate, sodium bicarbonate, sodium carbonate, sodium citrate, sodium borate and mixtures thereof.

18. The process according to claim 6 wherein the basic metal salt containing catalyst is present in an amount ranging from 1 to 20% by weight of the glycine or salt thereof.

19. The process according to claim 1 wherein the reaction resultant mass has a Hunter Lab Color Scale value of L ranging from 70 to 100.

20. The process according to claim 1 further comprising from 0 to 10% water.

21. The process according to claim 1 further comprising from 0 to 1% water.

* * * * *